United States Patent [19]

Riebel

[11] Patent Number: 5,250,685
[45] Date of Patent: Oct. 5, 1993

[54] PROCESS FOR THE PREPARATION OF S-ALKYL-ISOTHIOUREIDOAZINES

[75] Inventor: Hans-Jochem Riebel, Wuppertal, Fed. Rep. of Germany

[73] Assignee: Bayer Aktiengesellschaft, Leverkusen, Fed. Rep. of Germany

[21] Appl. No.: 949,181

[22] Filed: Sep. 21, 1992

[30] Foreign Application Priority Data

Sep. 19, 1991 [DE] Fed. Rep. of Germany ....... 4131136

[51] Int. Cl.$^5$ ............... C07D 251/42; C07D 251/48; C07D 251/54
[52] U.S. Cl. ..................... 544/199; 544/213; 544/210; 544/205; 544/320; 544/323; 544/332
[58] Field of Search ............ 544/213, 199, 210, 205, 544/320, 323, 332

[56] References Cited

U.S. PATENT DOCUMENTS 4,980,469 12/1990 Riebel et al. ............ 544/194
5,086,177 2/1992 Riebel et al. ............ 544/320

FOREIGN PATENT DOCUMENTS 0117014 1/1984 European Pat. Off. .
0358018 8/1989 European Pat. Off. .

OTHER PUBLICATIONS

Ricardo Bossio, *J. Heterocyclyl. Chem., Jul-Aug. 1958*, pp. 1147-1148.

*Primary Examiner*—John M. Ford
*Attorney, Agent, or Firm*—Sprung Horn Kramer & Woods

[57] ABSTRACT

A process for the preparation of an S-alkyl-isothioureidoazine of the formula

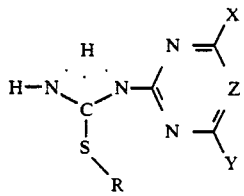

in which
R is alkyl,
X and Y each independently is selected from the group consisting of hydrogen, halogen, and alkyl, halogenoalkyl, alkoxyalkyl, halogenoalkoxy, alkoxy, alkylthio, halogenoalkylthio, alkylamino or dialkylamino, each of which is optionally substitued, and
Z is nitrogen or CH which comprises in a first step reacting an thioureidoazine of the formula

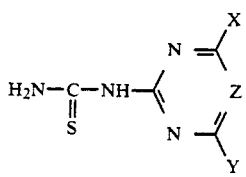

with a dialkyl sulphate of the formula

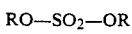

at a temperature between about 20° C. and 150° C., thereby to form an adduct of the formula

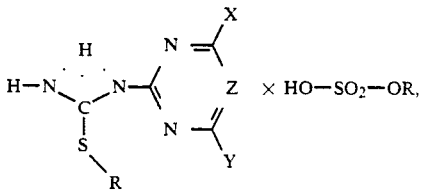

and in a second step reacting the adduct with an acid acceptor in the presence of an aprotic polar diluent at a temperature between about 0° C. and 50° C.

9 Claims, No Drawings

PROCESS FOR THE PREPARATION OF S-ALKYL-ISOTHIOUREIDOAZINES

The invention relates to a process for the preparation of known S-alkyl-isothioureidoazines which can be used as intermediates for the preparation of herbicides.

It is known that S-alkyl-isothioureidoazines are obtained when halogenoazines are reacted with S-alkyl-isothiuronium salts (cf. EP-A 117,014, Ex. 9). However, the yield in this preparation method is unsatisfactory.

It is furthermore known that S-alkyl-isothioureidoazines can also be prepared by reacting N-azinyliminodithiocarbonic acid diesters with ammonia (cf. EP-A 358,018, Ex. II-1). However, the preparation of the N-azinyliminodithiocarbonic acid diesters required as starting materials in this process, in which carbon disulphide is used, can be carried out on an industrial scale only with great difficulty.

Finally, it is known that alkylation of certain thioureidoazines with dimethyl sulphate to give corresponding S-methyl-isothioureidoazines is also possible (cf. J. Heterocycl. Chem. 22 (1985), 1147-1148). However, the solvent dimethylformamide which is used in this process has become virtually unacceptable for use in industry.

It has now been found that S-alkyl-isothioureidoazines of the general formula (I)

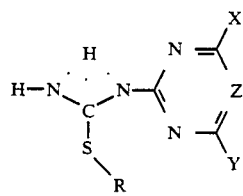

in which
R represents alkyl,
X and Y are identical or different and represent hydrogen, halogen or a radical from the series comprising alkyl, halogenoalkyl, alkoxyalkyl, halogenoalkoxy, alkoxy, alkylthio, halogenoalkylthio, alkylamino or dialkylamino, each of which is optionally substituted, and
Z represents nitrogen or a CH group,
are obtained in very good yields and in high purity when thioureidoazines of the general formula (II)

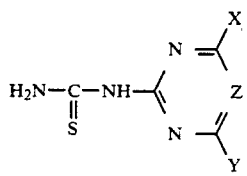

in which
X, Y and Z have the abovementioned meanings,
are reacted with dialkyl sulphates of the general formula (III)

$$RO-SO_2-OR \quad (III)$$

in which
R has the abovementioned meaning, if appropriate in the presence of an unpolar diluent, at temperatures between 20° C. and 150° C.,
and the adducts which have been formed in this process, of the formula (Ia)

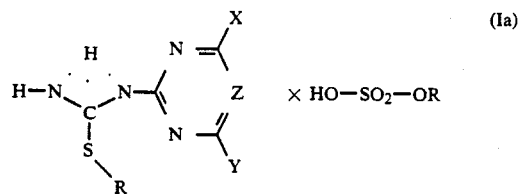

in which
R, X, Y and Z have the abovementioned meanings,
are reacted with an acid acceptor in the presence of an aprotic polar diluent at temperatures between 0° C. and 50° C., either after isolation or without intermediate isolation.

Surprisingly, the process according to the invention allows the compounds of the formula (I) to be prepared in high yields in a relatively simple manner.

The process according to the invention preferably relates to the preparation of S-alkyl-isothioureidoazines of the general formula (I) in which
R represents methyl or ethyl,
X and Y are identical or different and represent hydrogen, fluorine, chlorine, bromine, a radical from the series comprising $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_4$-alkylthio, $C_1$-$C_4$-halogenoalkylthio, $C_1$-$C_4$-alkylamino or di-($C_1$-$C_2$-alkyl)-amin o, each of which is optionally substituted, and
Z represents nitrogen or a CH group.

In particular, the process according to the invention relates to the preparation of compounds of the formula (I) in which
R represents methyl,
X represents hydrogen, chlorine, methyl, ethyl, trifluoromethyl, methoxy, ethoxy, difluoromethoxy, methylthio, ethylthio, methylamino, ethylamino or dimethylamino,
Y represents methyl, trifluoromethyl, methoxy, ethoxy or difluoromethoxy, and
Z represents nitrogen or a CH group.

If, for example, 4,6-dimethyl-2-thioureidopyrimidine and dimethyl sulphate and, in the subsequent step, sodium hydroxide are used as starting materials, the course of the reaction can be outlined by the following equation:

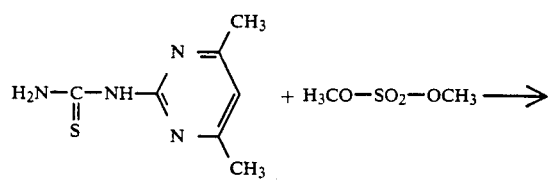

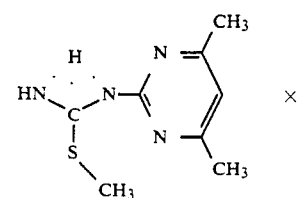

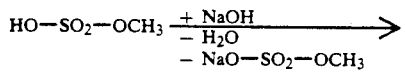

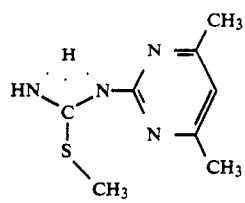

Formula (II) provides a general definition of the thioureidoazines to be used as starting materials. In formula (II), X, Y and Z preferably, or in particular, have the meaning which has already been mentioned above in connection with the description of the compounds of the formula (I) to be prepared according to the invention as being preferred, or particularly preferred, for X, Y and Z.

The starting materials of the formula (II) are known and/or can be prepared by processes known per se (cf. EP-A 173,313).

Formula (III) provides a general definition of the dialkyl sulphates furthermore required as starting materials. In formula (III), R preferably represents methyl or ethyl, in particular methyl.

The starting materials of the formula (III) are known chemicals for synthesis.

If appropriate, the first phase of the process according to the invention is carried out in the presence of an non-polar diluent. Suitable unpolar diluents are, preferably, aromatic, in particular benzenoid, hydrocarbons which, if appropriate, contain 1 to 3 alkyl substituents, each of which has 1 to 3 carbon atoms. Examples of these which may be mentioned are: benzene, toluene, o-, m- and p-xylene, ethylbenzene, propylbenzene, cumene, 1,2,3-trimethylbenzene, 1,2,4-trimethylbenzene and 1,3,5-trimethylbenzene. Toluene is very particularly preferred as diluent.

In the first phase of the process according to the invention, the reaction temperatures can be varied within a substantial range. In general, the process is carried out at temperatures between 20° C. and 150° C., preferably at temperatures between 50° C. and 120° C., in particular between 70° C. and 110° C.

The process according to the invention is generally carried out under atmospheric pressure. However, it is also possible to carry out the process under increased or reduced pressure.

Acid acceptors which can be employed in the second phase of the process according to the invention are all acid-binding agents which can customarily be used for reactions of this type. The following are preferably suitable: alkali metal hydrides and alkaline earth metal hydrides such as lithium hydride, sodium hydride, potassium hydride and calcium hydride, alkali metal hydroxides and alkaline earth metal hydroxides such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates such as sodium carbonate, sodium hydrogen carbonate, potassium carbonate or potassium hydrogen carbonate as well as calcium carbonate, alkali metal acetates such as sodium acetate and potassium acetate, alkali metal alcoholates such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo[5,4,0]-undec-7-ene (DBU) and 1,4-diazabicyclo-[2,2,2]octane (DABCO). Potassium carbonate is very particularly preferred as acid acceptor.

The reaction of the adducts of the formula (Ia) with an acid acceptor as the second phase of the process according to the invention is carried out in the presence of an aprotic polar diluent. Diluents which are preferably used in this context are ketones such as acetone, methyl ethyl ketone, methyl isopropyl ketone and methyl isobutyl ketone, esters such as methyl acetate and ethyl acetate, and also nitriles such as acetonitrile and propionitrile. Acetonitrile is very particularly preferred as diluent for the second phase of the process according to the invention.

In the second phase of the process according to the invention, the reaction temperatures can be varied within a substantial range. In general, the process is carried out at temperatures between 0° C. and 50° C., preferably at temperatures between 10° C. and 40° C., in particular between 20° C. and 30° C.

For carrying out the process according to the invention, between 1.0 and 1.5 moles, preferably between 1.05 and 1.25 moles, of a dialkyl sulphate of the formula (III) are generally employed per mole of thioureidoazine of the formula (II).

In general, the starting materials and if appropriate, the diluent, are combined at room temperature and the mixture is then brought to the reaction temperature required. When the reaction has ended, the mixture is cooled to room temperature (approx. 20° C.) again. If a diluent is used, the adduct of the formula (Ia) which is obtained in crystalline form can be isolated by filtration with suction. If not, the product is stirred with a diluent such as, for example, tert-butyl methyl ether and/or acetone, and filtered off with suction. When the first phase of the process according to the invention is carried out without a solvent, the crude product of the formula (Ia) can also be further reacted without intermediate isolation.

For carrying out the second phase of the process according to the invention, the adduct of the formula (Ia) is stirred for one or more hours with a diluent and an acid acceptor at the temperature required. The mixture is then filtered, and the diluent is carefully removed from the filtrate by distillation under reduced pressure. The product of the formula (I) is obtained as a crystalline residue.

The S-alkyl-isothioureidoazines of the formula (I) which are to be prepared by the process according to the invention can be used as intermediates for the preparation of herbicides (cf. EP-A 121,082 and EP-A 358,018).

PREPARATION EXAMPLES

Example 1

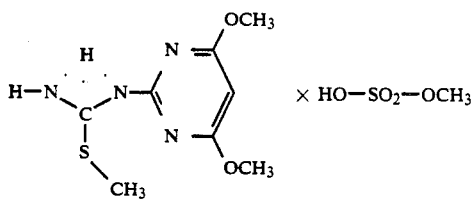

A mixture of 10.7 g (50 mmol) of 4,6-dimethoxy-2-thioureido-pyrimidine and 7.0 g (62 mmol) of dimethyl sulphate is heated for 30 minutes at 80° C. to 90° C. It is then cooled to 20° C., and the solid product is comminuted, stirred with tert-butyl methyl ether and filtered off with suction. The product is stirred with acetone and again subjected to filtration with suction.

15.6 g (92 % of theory) of 1:1 adduct of 4,6-dimethoxy-2-(S-methyl-isothioureido)-pyrimidine with monomethyl sulphate, of melting point 151° C., are obtained.

EXAMPLE 2

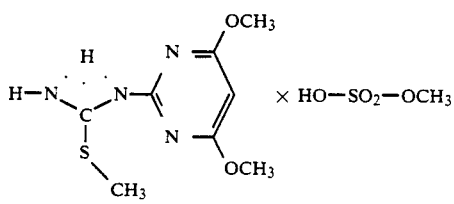

A mixture of 10.7 g (50 mmol) of 4,6-dimethoxy-2-thioureido-pyrimidine, 7.0 g (62 mmol) of dimethyl sulphate and 100 ml of toluene is heated for 60 minutes at 100° C. and then cooled to room temperature (20° C.). The crystalline product is isolated by filtration with suction.

15.7 g (92 % of theory) of 1:1 adduct of 4,6-dimethoxy-2-(S-methyl-isothioureido)-pyrimidine with monomethyl sulphate, of melting point 151° C., are obtained.

EXAMPLE 3

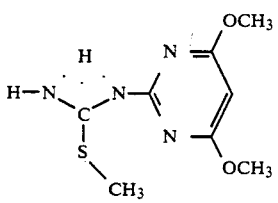

15 g (44 mmol) of 1:1 adduct of 4,6-dimethoxy-2-(S-methyl -isothioureido)-pyrimidine and monomethyl sulphate (preparation cf. Examples 1 and 2) in 100 ml of acetonitrile are stirred for 60 minutes at 22° C. with 6.6 g (47 mmol) of potassium carbonate. After filtration, the solvent is carefully removed from the filtrate by distillation under a water pump vacuum.

9.6 g (96 % of theory) of 4,6-dimethoxy-2-(S-methyl-isothioureido)-pyrimidine are obtained as a crystalline product of melting point 126° C.

EXAMPLE 4

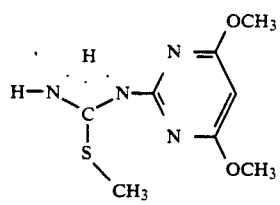

A mixture of 21.5 g (0.10 mol) of 4,6-dimethoxy-2-thioureido-pyrimidine and 11.2 g (0.10 mol) of dimethyl sulphate is heated for 30 minutes at 90° C. to 100° C. After cooling to 20° C., 200 ml of acetonitrile are added to the product of this reaction, and the mixture is stirred for 30 minutes. 15 g (0. 11 mol) of potassium carbonate are then added thereto, and the mixture is stirred for 4 hours at 22° C. The mixture is then filtered, and the diluent is carefully removed from the filtrate by distillation under a water pump vacuum.

17.8 g (78 % of theory) of 4,6-dimethoxy-2-(S-methyl-isothioureido)-pyrimidine are obtained as a crystalline product of melting point 125° C.

It will be appreciated that the instant specification and claims are set forth by way of illustration and not limitation, and that various modifications and changes may be made without departing from the spirit and scope of the present invention.

I claim:

1. A process for the preparation of an S-alkyl-isothioureidoazine of the formula

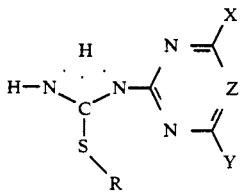

in which

R is methyl or ethyl,

X and Y each independently is selected from the group consisting of hydrogen, halogen, $C_1$-$C_4$-alkyl, $C_1$-$C_4$-halogenoalkyl, $C_1$-$C_2$-alkoxy -$C_1$-$C_2$-alkyl, $C_1$-$C_4$-alkoxy, $C_1$-$C_4$-halogenoalkoxy, $C_1$-$C_4$-alkylthio, $C_1$-$C_4$-halogenoalkylthio, and $C_1$-$C_4$-alkylamino or di-($C_1$-$C_2$-alkyl)-amino, and Z is nitrogen or CH which comprises in a first step reacting an thioureidoazine of the formula

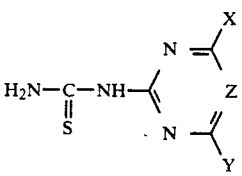

with a dialkyl sulphate of the formula

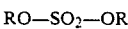

at a temperature between about 20° C. and 150° C., thereby to form an adduct of the formula

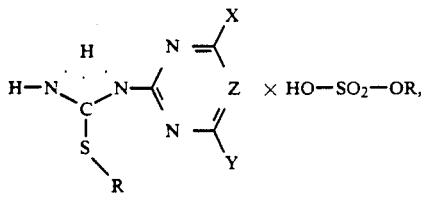

and in a second step reacting the adduct with an acid acceptor in the presence of an aprotic polar diluent at a temperature between about 0° C. and 50° C.

2. A process according to claim 1, in which
R is methyl,
X is hydrogen, chlorine, methyl, ethyl, trifluoromethyl, methoxy, ethoxy, difluoromethoxy, methylthio, ethylthio, methylamino, ethylamino or dimethylamino, and
Y is methyl, trifluoromethyl, methoxy, ethoxy or difluoromethoxy.

3. A process according to claim 1, wherein the first step is carried out at a temperature between about 50° C. and 120° C. and the second step at a temperature between about 10° C. and 40° C.

4. A process according to claim 1, wherein the first step is carried out at a temperature between about 70° C. and 110° C. and the second step at a temperature between about 20° C. and 30° C.

5. A process according to claim 1, wherein about 1 to 1.5 moles of dialkyl sulphate of the formula (III) are employed per mole of thioureidoazine of the formula (II).

6. A process according to claim 1, wherein the first step is carried out in the presence of a non-polar diluent.

7. A process according to claim 1, wherein the aprotic polar diluent in the second step of the process is acetonitrile.

8. A process according to claim 1, wherein the acid acceptor employed in the second step is potassium carbonate.

9. A process according to claim 2, wherein the first step is carried out at a temperature between about 70° C. and 110° C. in the presence of toluene, about 1 to 1.5 employed per mole of thioureidoazine of the formula (II), and the product of the first step is isolated and reacted in the second step at a temperature between about 20° C. and 30° C. in acetonitrile as the aprotic polar diluent with potassium carbonate as acid acceptor.

* * * * *